United States Patent [19]

Kameyama

[11] Patent Number: 5,707,339
[45] Date of Patent: Jan. 13, 1998

[54] METHOD OF DIRECTLY FREEZING PORCINE EMBRYOS

[75] Inventor: Kenji Kameyama, Ibaraki-ken, Japan

[73] Assignee: The Japanese Research Association for Animal Embryo Transfer Technology, Tokyo, Japan

[21] Appl. No.: 590,760

[22] Filed: Jan. 24, 1996

[30] Foreign Application Priority Data

Oct. 30, 1995 [JP] Japan .................................. 7-281911

[51] Int. Cl.$^6$ .................................................. A61B 17/43
[52] U.S. Cl. .................. 600/34; 600/33; 435/1.3; 435/2; 435/240.2
[58] Field of Search ................ 600/33–35; 623/15; 128/898; 435/1.3, 2, 240.2

[56] References Cited

U.S. PATENT DOCUMENTS 5,336,616   8/1994   Livesey et al. .
5,504,002   4/1996   Aoyagi ................................ 600/34 X

FOREIGN PATENT DOCUMENTS

WO 91/12719   9/1991   WIPO .
WO 95/05075   2/1995   WIPO .

OTHER PUBLICATIONS

Nagashima et al., "Recent Advances in Cryopreservation of Porcine Embryos", Theriogneology, vol. 41, pp. 113–118, (1994).

Nagashima et al., "Cryopreservation of Porcine Embryos", Scientific Correspondence, Nature, vol. 374, p. 416, (1995).

*Primary Examiner*—Jennifer Bahr
*Assistant Examiner*—Ryan Carter
*Attorney, Agent, or Firm*—Foley & Lardner

[57] ABSTRACT

A method of directly freezing porcine embryos which includes adding a solution to be frozen including ethylene glycol, propylene glycol, bovine serum and dextran in the presence of basic medium to porcine embryos and freezing the resulting mixture.

9 Claims, 1 Drawing Sheet

METHOD OF DIRECTLY FREEZING PORCINE EMBRYOS

BACKGROUND OF THE INVENTION

The present invention relates to a method of directly freezing porcine embryos. Additionally, the invention relates to a method of reproducing a pig by using the frozen embryos which are capable of directly transferring without checking the embryos.

DESCRIPTION OF THE RELATED PRIOR ART

Although the transfer of porcine embryos has been noticed as a new reproduction technique such as increased rate of reproduction and production of cleaned pig, such techniques are hardly utilized from some reasons. The main reasons for inhibiting a practical use of the transfer of porcine embryos are based on the fact that non-surgical removal and a transfer of embryos are very difficult because of the complicated structure of its reproductive organ and the embryo cannot be preserved because of its instability at a lower temperature.

In the reproduction field of bovine, a cryopreserving technique which is a semi-permanental preserving method of embryos has been already affirmed and the transfer of embryos is widely employed as a practical technique. However, the viability of porcine embryos may lower not only at a preservation temperature under freezing, but also exposure to a lower temperature and the transfer of porcine embryos is restricted by time and distance. Piglets based on the transfer of cryopreserved embryos have been first produced in the world in the National Institute of Animal Industry on 1989 (Oguri, The 53th Meeting of the Japanese Society of Swine Science 48–54, 1990). Since then, piglets were produced in two facilities in Japan, but a success leading to growth is highly low and their reproductivity is practically nothing. Until now, in a conventional step-wise method, there are only 5 success examples in the world and the number of the born piglets was several head, ie, 10 several % per thawed embryos (Oguri, The 53th Meeting of the Japanese Society of Swine Science, 48–54, 1990; Kameyama et al., The 78th Meeting of the Japanese Society of Animal Reproduct I-57, 1990; Kashiwazaki et al., ibid., I-57, 1990; Nagashima et al., Theriogenology, 41: 113–118, 1994 and Nagashima et al., Nature, 374: 416, 1995). From such a reason, a transfer has been carried out by thawing many embryos to remove a cryoprotectant, and selecting the thawed embryos. By a step-wise method is meant a method of transferring an embryo which comprises freezing an embryo in a straw in the presence of a glycerin and the like as a cryoprotectant, removing it from the straw after thawing the frozen embryo at the transfer stage, and discharging the cryoprotectant at the intervals of 3–5 times; said method being also named as a step dilution method.

A cryoprotectant method of a pig embryo has not established unlike that of a bovine embryo. Thus, the cryoprotected embryos thereof could not be utilized for maintenance of a family line produced pig and the transfer of pigs. Accordingly, the object of the present invention is to establish a method of cryoprotecting a porcine embryo.

The present inventor has discovered a method of transferring directly a porcine embryo which comprises adding a dextran, serum, ethylene glycol and propylene glycol to the porcine embryo in the presence of a basic medium and freezing it.

BRIEF DESCRIPTION OF THE DRAWING

There is given a cross-sectional view of a straw enclosing a porcine embryo according to the present invention.

In the accompanying drawing:

A straw

B cotton plug

C solution to be frozen

D air

E solution to be frozen+embryo

F seal

DESCRIPTION OF THE PREFERRED EMBODIMENTS

Figure 1:
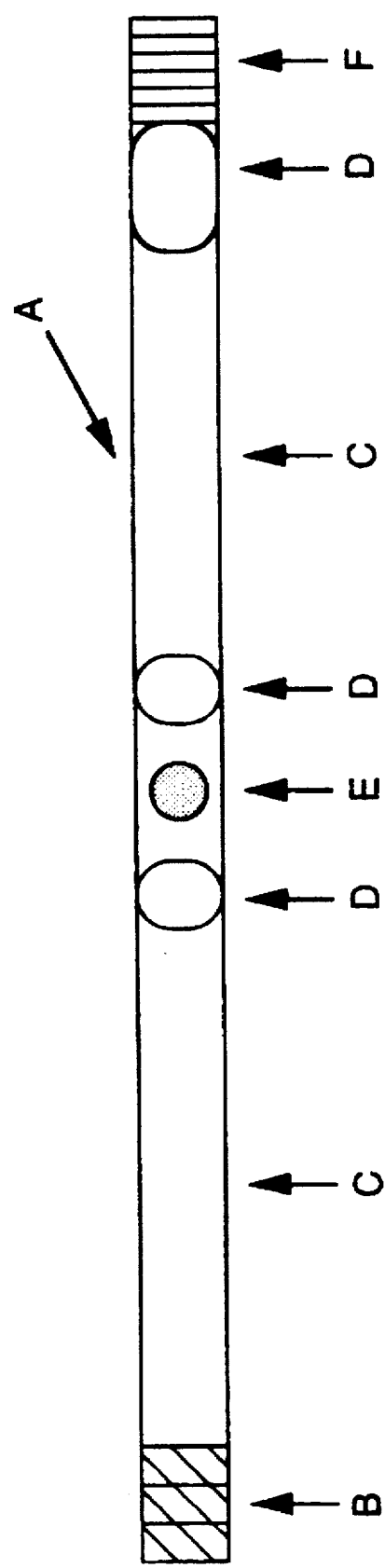

The present invention is further illustrated with the following examples.

EXAMPLE 1

(1) Solution to be frozen:

Embryos in the expanded blastocyst stage which have been recovered on 6th day from artificial fertilization at estrus were employed. The composition of the solution to be frozen which can be directly transferred in which a supplemented calf serum (which is one adjusted in components by adding various growth factors and minor elements; Calf Supreme™ manufactured by Gibco being used in Example) and dextran have been added in the cryoprotectant is as follows:

4% (v/v): ethylene glycol

4% (v/v): propylene glycol

20% (v/v): supplemented calf serum

1% (w/v): dextran basic medium: TCM 199

(2) Container for freezing:

A 0.5 ml plastic straw (3) Method for insertion into the straw:

As shown in FIG. 1, the following components were inserted so as to be located in the numerical order from the cotton plug end in the straw.

1. the solution to be frozen 2. air 3. the solution to be frozen and embryos 4. air 5. the solution to be frozen (4) Program freezer:

manufactured by Tokyo Rika (5) Ice seeding temperature:

−6° C.

(6) Cooling rate:

0.5° C./minute (7) Temperature at the immersion in liquid nitrogen:

−32.5° C.

(8) Thawing method:

The straw was taken out of liquid nitrogen, held in air (at room temperature) for 5 to 10 seconds, and then thawed in water at 35° C.

(9) Transferring method:

The whole contents in the straw were discharged in an incubation dish and embryos were set in a catheter, followed by transfer.

The comparison between the present method and conventional method is shown in Table 1.

TABLE 1

| Method | Solution to be frozen | Thawing method |
|---|---|---|
| Conventional method (step-wise method) | 10% glycerol + 20% supplemented calf serum (SCM) or fetus calf serum (FCS) + 1% dextran, basic medium PBS or TCM 199 | 5 steps (6.7%, 3.3%, 0% glycerol + 0.3M sucrose + 20% SCM or 0.2M, 0.1M sucrose + 20% SCM or FCS |
| Method of the Invention (Direct method) | 4% ethylene glycol + 4% propylene glycol + 20% supplemented calf serum + 1% dextran, basic medium TCM 199 | Direct transfer |

The results are shown in Table 2.

TABLE 2

Transfer results of cryopreserved pig embryos

| Number | Method | Number of thawed embryos | Number of transferred embryos (thawed embryos %) | Number of delivery transferable embryos % | Number of delivery thawed embryos % | Remark |
|---|---|---|---|---|---|---|
| 1 | SW-1 | 37 | 20 (54%) | 4 (20%) | 11% | still-birth 1 mummy 1 |
| 2 | SW-2 | 50 | 20 (38%) | 5 (25%) | 5% | |
| 3 | SW-3 | 35 | 20 (57%) | 0 (0%) | 0% | no conc |
| 4 | Direct method | 20 | 20 (100%) | 10 (50%) | 50% | still-birth |
| 5 | SW-3 | 49 | 20 (41%) | 2 (10%) | 4% | |
| 6 | Direct method | 20 | 20 (100%) | 1 (5%) | 5% | |

Notes:
SW-1 basic medium PBS, FCS, lecithin added
SW-2 basic medium PBS, FCS, tocopherol added
SW-3 basic medium TCM 199, SCS
Direct method (the process of the present invention) after thawing the embryos, the solution is removed into a catheter for transfer and then transferred.

I claim:

1. A method of freezing a porcine embryo which comprises freezing a porcine embryo in a solution comprising ethylene glycol, propylene glycol, bovine serum, dextran and a basic medium.

2. A method according to claim 1, wherein the concentration of dextran is about 1% (w/v).

3. A method according to claim 1, wherein the concentration of bovine serum is about 20% (v/v).

4. A method according to claim 1, wherein said bovine serum comprises supplemented calf serum.

5. A method according to claim 1, wherein the concentration of dextran in said solution is about 1% (w/v).

6. A method according to claim 1, wherein the concentration of bovine serum in said solution is about 20% (v/v).

7. A method of propagating a pig which comprises freezing a porcine embryo in a cryoprotectant solution comprising bovine serum, ethylene glycol, propylene glycol, and dextran, thereby forming a frozen porcine embryo, thawing the frozen porcine embryo and transferring the thawed porcine embryo to a recipient animal.

8. A method of freezing a porcine embryo which comprises freezing a porcine embryo in a cryoprotectant solution comprising bovine serum, ethylene glycol, propylene glycol, and dextran.

9. A method according to claim 8, wherein said bovine serum comprises supplemented calf serum.

* * * * *